US006598474B2

(12) United States Patent
Purpura et al.

(10) Patent No.: US 6,598,474 B2
(45) Date of Patent: Jul. 29, 2003

(54) ADAPTER FOR HOLDING A SAMPLE CONTAINER TO FACILITATE SENSING OF LIQUID LEVEL IN THE SAMPLE CONTAINER

(75) Inventors: Paul E. Purpura, Yorktown, NY (US); Thomas W. De Young, Stormville, NY (US)

(73) Assignee: Bayer Corporation, Tarrytown, NY (US)

( * ) Notice: Subject to any disclaimer, the term of this patent is extended or adjusted under 35 U.S.C. 154(b) by 0 days.

(21) Appl. No.: 10/277,521

(22) Filed: Oct. 21, 2002

(65) Prior Publication Data

US 2003/0037611 A1 Feb. 27, 2003

Related U.S. Application Data

(62) Division of application No. 09/798,700, filed on Mar. 2, 2001.

(51) Int. Cl.⁷ .......................... B01L 3/00; G01N 37/00; G08B 21/00; G05D 9/00
(52) U.S. Cl. .................. 73/290 V; 73/864.83; 73/864.91; 340/621; 422/106; 220/495.01
(58) Field of Search ............... 73/864.83, 864.91, 73/864.51; 340/290 V, 621; 422/106, 104; 220/495.01, 618; 211/74; 435/304.01

(56) References Cited

U.S. PATENT DOCUMENTS

| | | | |
|---|---|---|---|
| 2,325,224 A | | 7/1943 | Bryant, Sr. |
| 2,458,737 A | | 1/1949 | Salkowitz |
| 2,677,373 A | | 4/1954 | Barradas |
| 3,655,090 A | | 4/1972 | Rothrock et al. |
| 3,807,955 A | | 4/1974 | Note, Jr. et al. |
| 3,913,564 A | * | 10/1975 | Freshley .................. 600/572 |
| 3,918,435 A | * | 11/1975 | Beall et al. .............. 600/572 |
| 4,221,004 A | * | 9/1980 | Combs et al. ............ 367/114 |
| 4,437,497 A | * | 3/1984 | Enander .................... 141/1 |
| 4,944,924 A | * | 7/1990 | Mawhirt et al. .......... 422/104 |
| 5,137,693 A | * | 8/1992 | Mawhirt .................. 422/104 |
| 5,316,146 A | | 5/1994 | Graff |
| 5,358,116 A | | 10/1994 | Brintazzoli |
| 5,393,497 A | | 2/1995 | Haber et al. |
| 5,515,995 A | | 5/1996 | Allen et al. |
| 5,579,929 A | | 12/1996 | Schwartz |
| 5,669,502 A | | 9/1997 | Ong et al. |
| 5,842,374 A | * | 12/1998 | Chang ..................... 73/290 R |
| 5,915,583 A | * | 6/1999 | Cloonan et al. .......... 220/23.86 |
| 5,924,594 A | | 7/1999 | Kelly |
| 6,043,097 A | * | 3/2000 | Dumitrescu et al. ...... 436/48 |
| 6,158,587 A | | 12/2000 | Emery |

FOREIGN PATENT DOCUMENTS

| | | |
|---|---|---|
| EP | 0 295 047 A2 | 12/1988 |
| EP | 0 469 390 A2 | 2/1992 |
| FR | 2 609 880 A1 | 7/1988 |

\* cited by examiner

Primary Examiner—Helen Kwok
Assistant Examiner—Katina Wilson
(74) Attorney, Agent, or Firm—Andrew L Klawitter; John M. Paolino; Rodman & Rodman

(57) ABSTRACT

An adapter for holding a sample container includes a main body portion and a tapered body portion that forms a continuation of the main body portion. The tapered body portion includes a mouth opening that is of lesser diameter than the diameter of the main body portion. The mouth opening of the adapter is sized to provide direct support of a sample container which holds a liquid sample. During liquid level sensing ultrasonic waves from an ultrasound detector are reflected back to the sound detector as echoes from the lip flange of the sample container and from the liquid level within the sample container. The tapered surface of the adapter deflects sound echoes away from the sound detector. The adapter is thus invisible to the ultrasound detector. The echo from the liquid level is a variable duration echo and the echo from the lip flange of the sample container is a fixed duration echo that is always of lesser duration than the variable duration echo. Thus the sound detector can easily recognize the liquid level echo and convert the characteristics of the liquid level echo to a discernible liquid level.

1 Claim, 9 Drawing Sheets

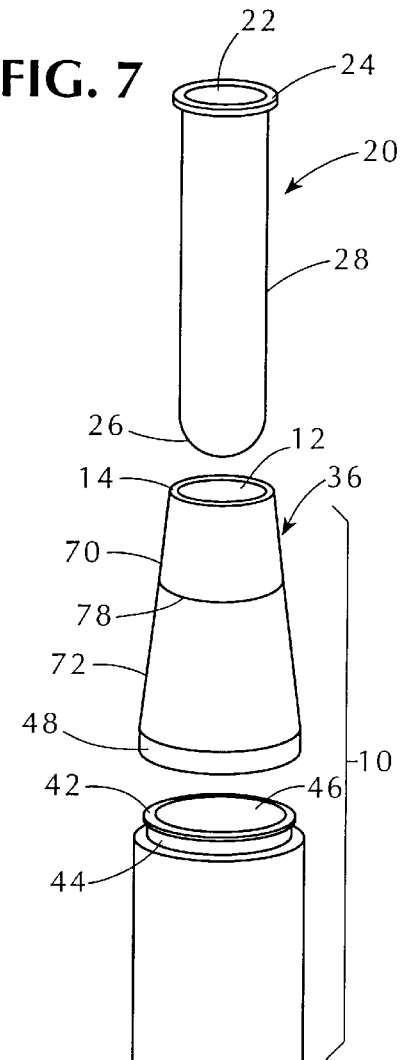
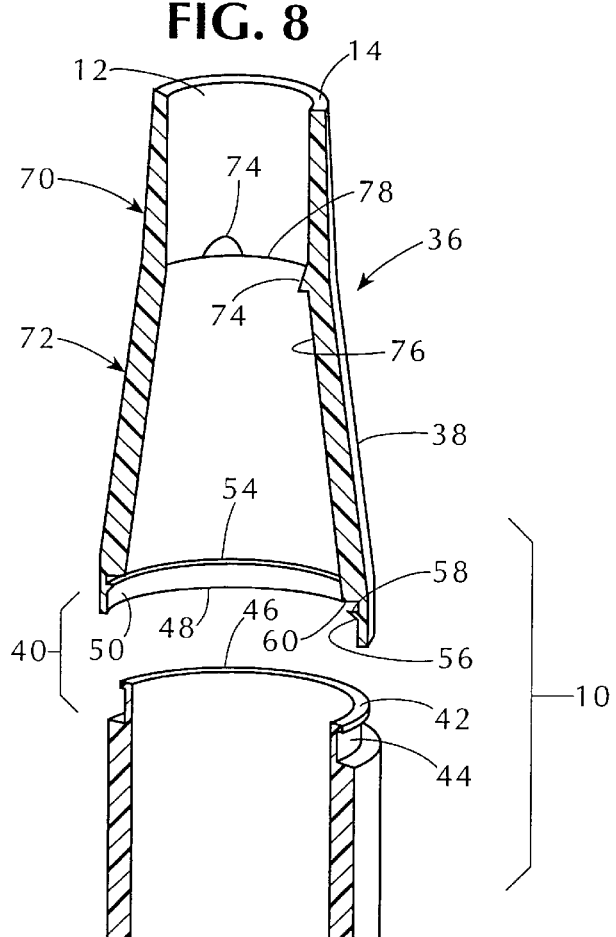
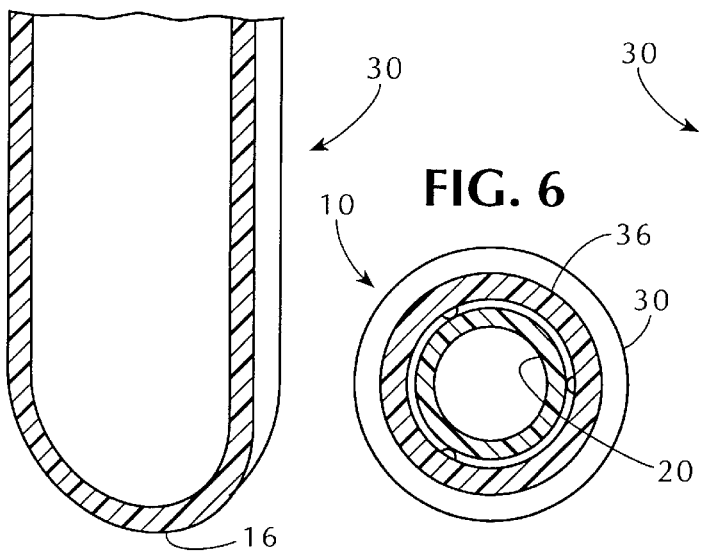

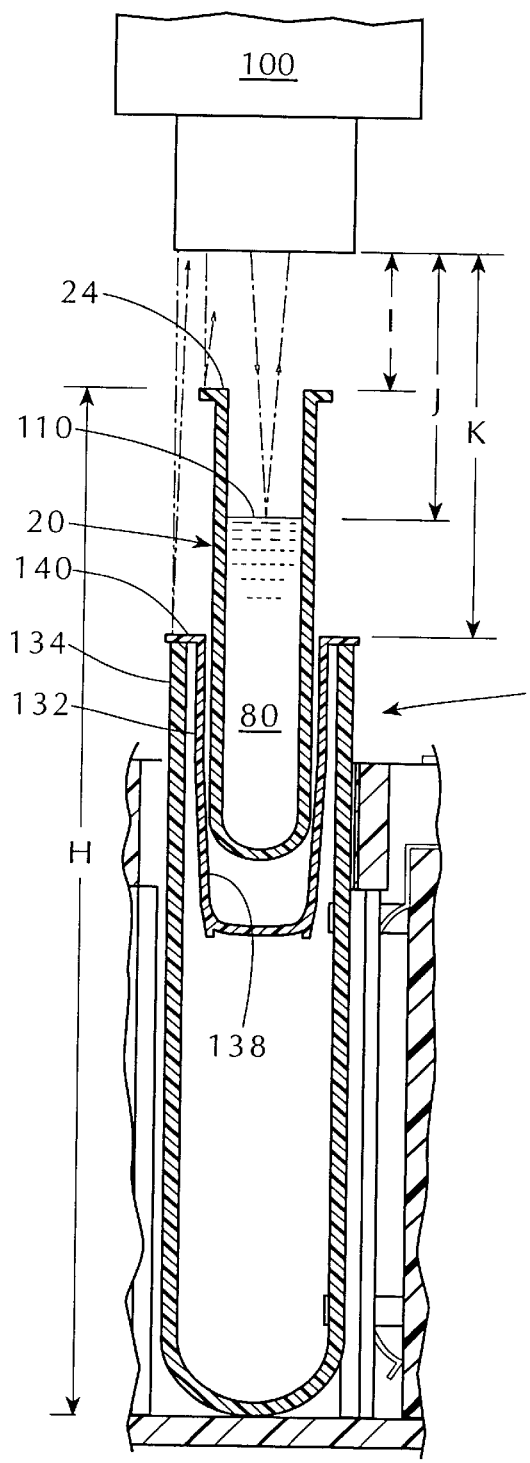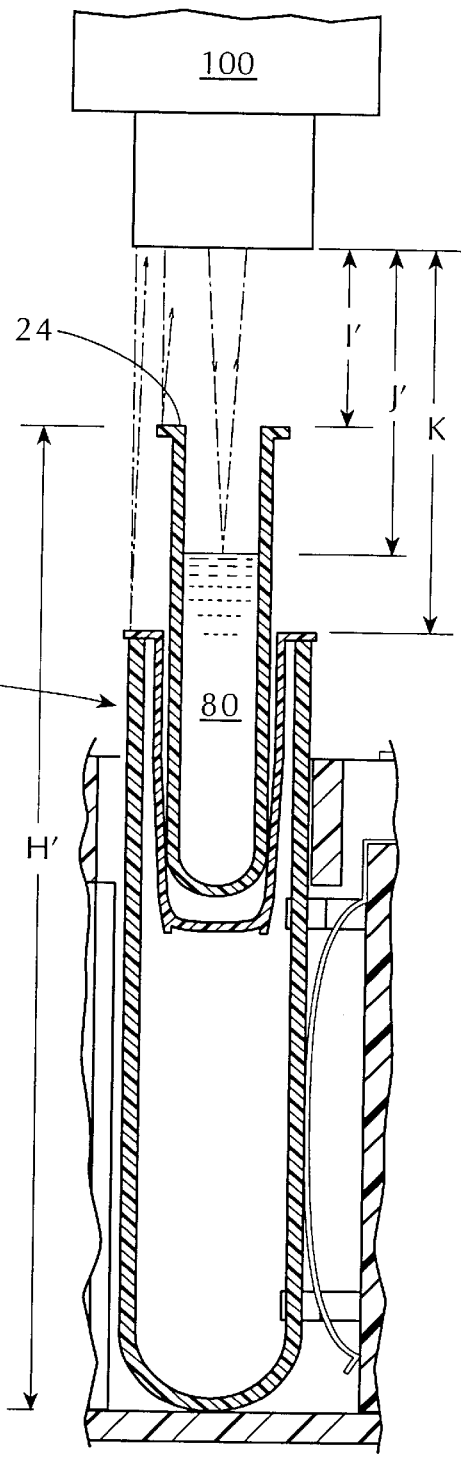

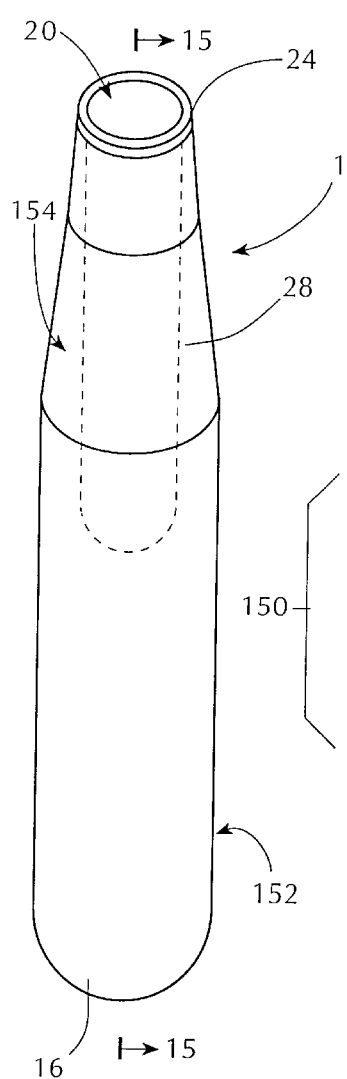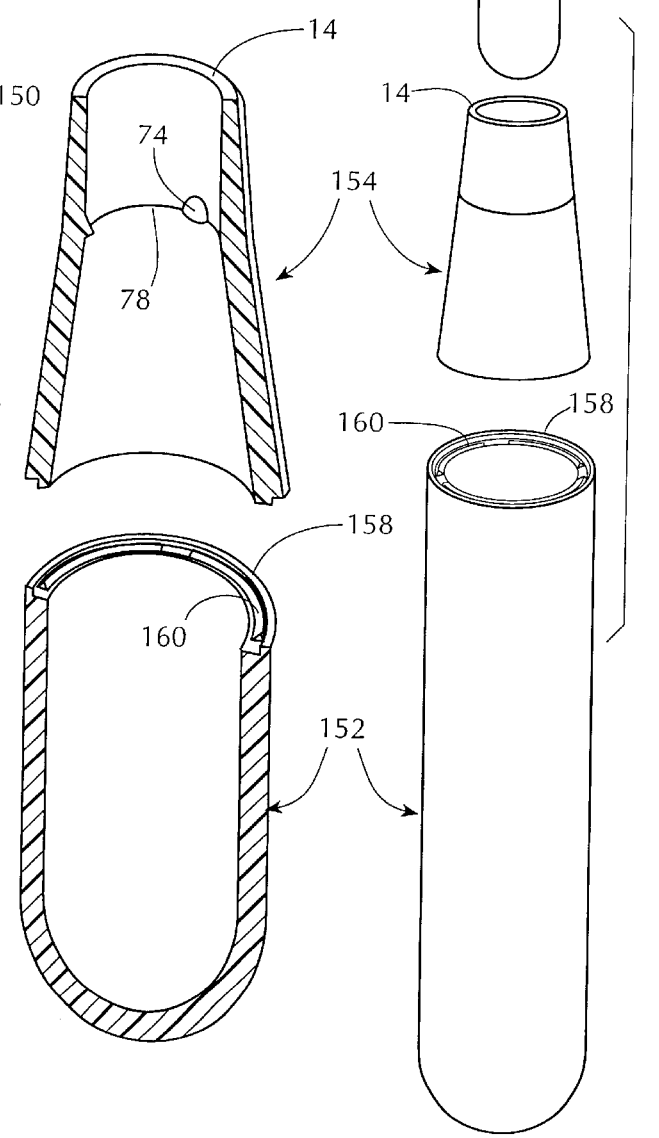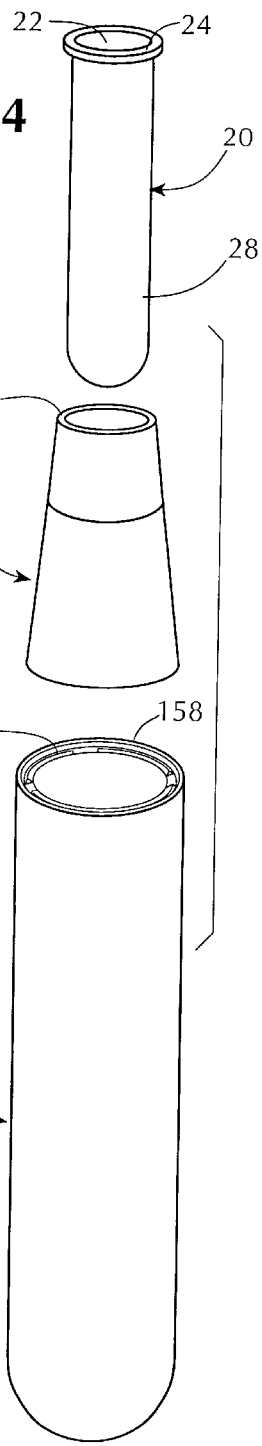

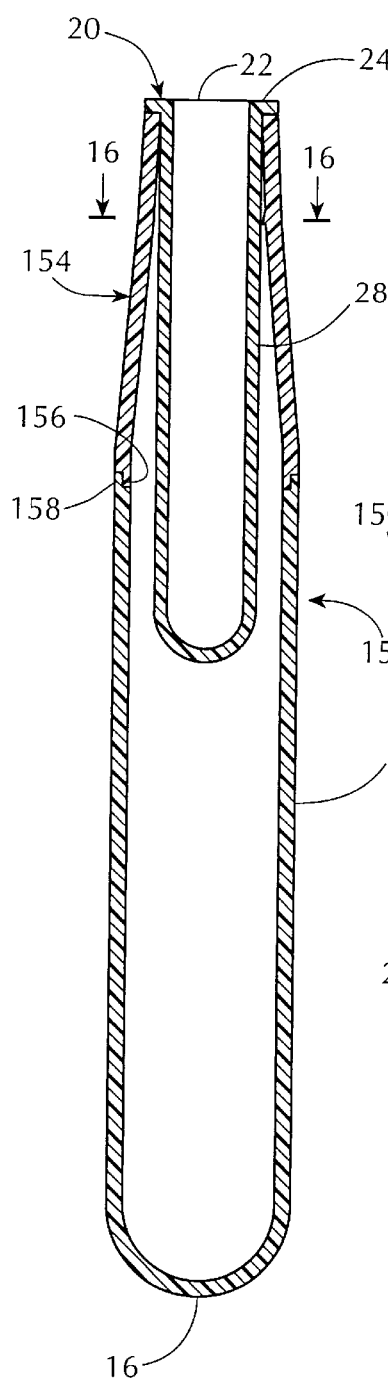
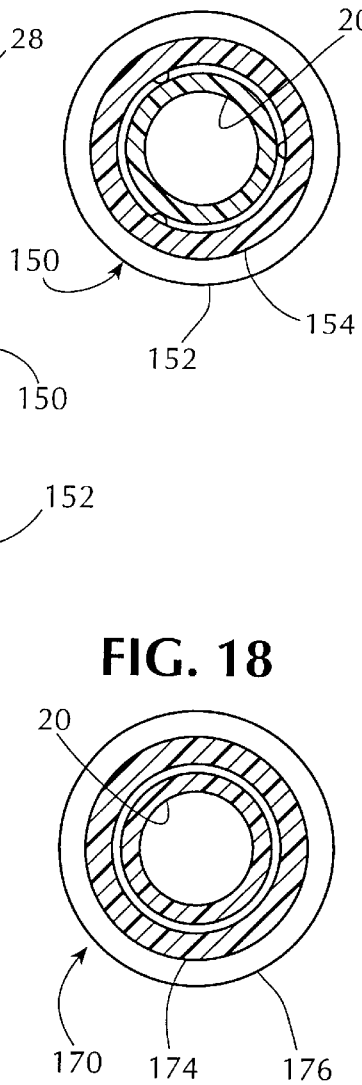
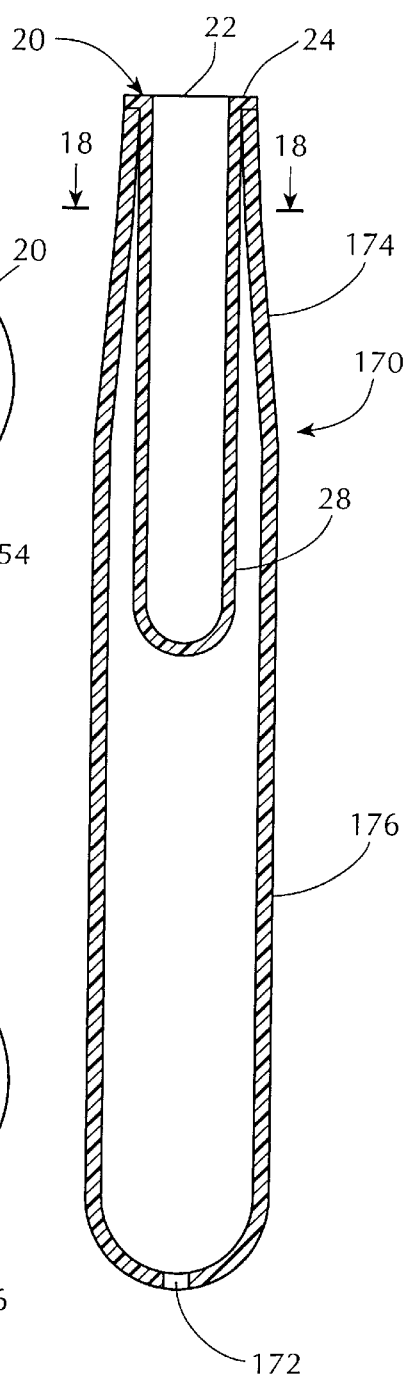

ADAPTER FOR HOLDING A SAMPLE CONTAINER TO FACILITATE SENSING OF LIQUID LEVEL IN THE SAMPLE CONTAINER

This application is a divisional application of U.S. patent application Ser. No. 09/798,700, filed Mar. 2, 2001, now pending in the U.S. Patent and Trademark Office.

BACKGROUND OF THE INVENTION

This invention relates to automatic sensing of liquid level in a sample container, and more particularly to a novel adapter for holding a sample container to facilitate liquid level sensing, and a novel method of sensing liquid level in a sample container.

Ultrasonic liquid level sensing is often used in automatic sample analysis systems of the type disclosed in U.S. Pat. Nos. 5,268,167 and 5,399,497. During automated sample analysis a liquid sample, such as blood serum, is subjected to a variety of tests. The serum sample, which is used as a source material for the tests, is usually placed in a relatively small container of fixed diameter, such as a Microtainer® tube, since the desired tests can be performed with relatively small amounts of diluted sample. For each discrete test on the serum a selected amount of diluted sample is aspirated from the sample container and combined with a predetermined amount of reagent to produce a chemical reaction that corresponds to a distinctive test on the sample.

The sample tests provide chemical information relating to different characteristics of the blood to assist in determining the health or well being of the individual being tested.

The quantity of sample which is used in each reagent test must be precisely controlled because test interpretation is based on an expectation that a predetermined amount of sample is combined with a predetermined amount of reagent. One known way of ensuring that the reagent tests are based on selected amounts of sample and reagent is to measure the sample level in a sample container before and after each aspiration of sample and to perform corresponding measurements on the reagent in a reagent container.

The liquid level measurement information will confirm that the intended amount of sample has in fact been used in a specific test. Thus consecutive measurements of sample level in a sample container provide confirmation that the required amount of liquid is removed from the sample container for each test. The sample level measurements for each test also provide an ongoing determination of the amount of liquid that remains in the sample container.

In known sample analysis systems of the type previously referred to it is common practice to transport one or more sample containers to different locations in the sample analysis system. Sample containers are usually transported in sample tube racks that carry larger diameter tubes than the Microtainer® tube, such as Vacutainer® tubes which have other uses in the sample analysis system. The sample tube rack preferably maintains tubes of all sizes in an upright position since the tubes are often in an open condition.

In order to simultaneously transport relatively small sample containers, such as Microtainer® tubes with other larger diameter tubes, each Microtainer® tube is usually supported in a larger diameter tube. However, because of a great disparity in size between the Microtainer® tube and the Vacutainer® tube it is necessary to cradle the Microtainer® tube in an intermediate holding device such as an Easi-nest® holder.

The Easi-nest® holder, which is open at one end and closed at the opposite end, has a tapered inside surface that is sized to bear against the Microtainer® tube when the Microtainer® tube is pushed into the Easi-nest® holder. The Easi-nest® holder also has a flange at the mouth portion that is large enough to rest on the mouth portion of the Vacutainer® tube. The support of a Microtainer® tube in an Easi-nest® holder held in a Vacutainer® tube is referred to herein as a sample tube support system or a Microtainer® tube support system.

The sensing of liquid level in the Microtainer® tube can be accomplished while the Microtainer® tube is supported in an Easi-nest® holder and elevated in a Vacutainer® tube held in a test tube rack or sample tube rack.

One known method of sensing liquid level is to employ an ultrasound detector. The ultrasound detector is located at a predetermined elevation over the travel path of the sample tube rack that holds the Microtainer® tube support system.

During liquid level sensing the ultrasound detector emits an ultrasonic wave directed against a horizontal surface of the Microtainer® tube support system that is proximate the liquid level. The ultrasonic wave is reflected as a sound echo from the horizontal surface back to the ultrasound detector. The characteristics of the echo are interpreted in a known manner by the ultrasound detector to indicate the distance between the ultrasound detector and the surface that reflected or produced the echo.

If the echo producing surface is in fact the liquid level in the Microtainer® tube than the distance between the liquid surface and the ultrasound detector can be determined by measuring the duration of time between the emission of the ultrasound wave and the receipt of the echo from the liquid level.

However, when a sample rack includes a Microtainer® tube supported in an Easi-nest® holder and a Vacutainer® tube it is difficult to selectively direct an ultrasonic wave against only the liquid level in the Microtainer® tube. To deal with this problem an ultrasonic wave is periodically emitted as the sample rack passes under the ultrasound detector. Ultrasonic waves are thus sequentially directed against other horizontal surfaces of the Microtainer® tube support system in addition to the liquid level. These horizontal surfaces include the mouth portion of the Microtainer® tube and the mouth portion of the Easi-nest® holder.

Based on a known height of the mouth portion of the Microtainer® tube from a reference level we can determine a first distance between the ultrasound detector and the mouth portion of the Microtainer® tube. Also based on a known height of the mouth portion of the Easi-nest® holder from the reference level we can determine a second distance between the ultrasound detector and the mouth portion of the Easi-nest® holder. Thus the mouth portion surfaces of the Microtainer® tube and the Easi-nest® holder can be identified from their corresponding echoes. The remaining echo would thus be associated with the liquid level in the Microtainer® tube.

Generally the liquid level 110 in a Microtainer® tube 20 is initially at a higher level than the mouth portion 140 of the Easi-nest® holder 132 (see FIGS. 10 and 11). However, as liquid 80 is depleted from the Microtainer® tube 20 the liquid level 110 recedes toward the mouth level 140 of the Easi-nest® holder 132. When liquid level 110 in the Microtainer® tube 20 closely approaches the level of the mouth portion 140 of the Easi-nest® holder 132 it becomes difficult to distinguish between the echo from the liquid level 110 in the Microtainer® tube 20 and the echo from the mouth portion 140 of the Easi-nest® holder 132. Thus there is a range of liquid level 110 in the Microtainer® tube 20 that can be confused with the level of the mouth portion 140 of the Easi-nest® holder 132 which can lead to errors in liquid level sensing.

It is thus desirable to provide a sample tube support structure for a sample container such as a Microtainer® tube that facilitates distinguishing a liquid level surface echo from an echo produced by a structural surface of the Microtainer® tube support system.

Another problem in measuring liquid level in a Microtainer® tube supported in an Easi-nest® holder is that the amount by which a Microtainer® tube projects from an Easi-nest® holder may vary due to manufacturing tolerances. Inconsistent positioning of the Microtainer® tube in the Easi-nest® holder is also common because the Microtainer® tube is usually manually pushed into snug engagement with the tapered surface of the Easi-nest® holder and there is no fixed stop position for the Microtainer® tube in the Easi-nest® holder. It is thus desirable to provide a Microtainer® tube support system wherein the Microtainer® tube is always located in the same position in the support system.

OBJECTS AND SUMMARY OF THE INVENTION

Among the several objects of the invention may be noted the provision of a novel support system or adapter for holding a sample tube container or Microtainer® tube in a sample rack to facilitate liquid level sensing in the sample container, a novel adapter for holding a sample container to facilitate liquid level sensing in the sample container by an ultrasound detector, a novel adapter having a reduced diameter mouth portion to provide direct support for a sample container, a novel adapter for direct support of a sample container without an intermediate support device between the sample container and the adapter, a novel adapter that directly supports a sample container at a lip flange of the sample container, a novel adapter having a body structure that diverts ultrasound wave echoes away from the ultrasound detector, a novel adapter having a body portion with a tapered section to divert ultrasonic wave echoes away from the ultrasound detector, a novel adapter that holds a sample container and is substantially invisible to an ultrasound detector to enable the ultrasound detector to receive only the sound echoes from the lip flange of the sample container and from the liquid level in the sample container and not receive echoes from any other structure of the sample tube support system, and a novel method of ultrasonically sensing liquid level in a sample container.

Other objects and features of the invention will be in part apparent and in part pointed out hereinafter.

In accordance with the invention an adapter for holding a sample container is a generally tubular structure having a main body portion and a tapered body portion. The main body portion preferably has a fixed diameter. The tapered body portion extends from the main body portion to a mouth opening that is of lesser diameter than the main body portion. The tapered body portion has an outer diameter that increases in magnitude in a direction from the mouth opening toward the main body portion.

The mouth opening of the adapter is sized to receive a relatively small diameter sample container such that a lip portion or lip flange of the sample container rests upon the mouth opening of the adapter. The tapered body portion of the adapter includes inner surface projections that bear slightly against the sample container when it is received in the mouth opening of the adapter.

In some embodiments of the invention the adapter is formed as a two piece stricture with one component being the tapered body portion and the other component being the main body portion.

In another embodiment of the invention the adapter has an enlarged bottom opening. The adapter can thus be formed as a one piece integral structure.

In one embodiment of the invention the main body portion and the tapered body portion are joined together at a snap fit joint. The snap fit joint includes a first lip that projects radially outwardly of the one of the main body portion and the tapered body portion and a second lip that projects radially inwardly of the other of the main body portion and the tapered body portion. Thus the main body portion and the tapered body portion can bypass each other with slight interference to permit one the lips to bypass the other lip to form an inseparable snap fit joint between the main body portion and the tapered body portion.

In a further embodiment of the invention the main body portion and the tapered body portion are joined together at complementary shaped step portions formed at the joint.

In some embodiments of the invention the bottom portion of the adapter has a curved semi-spherical shape.

In several embodiments of the invention the tapered body portion of the adapter has two distinct tapered sections. One of the two tapered sections has a lesser amount of slope than the other tapered section. Preferably the tapered section with the lesser amount of slope includes the mouth opening of the adapter.

When a sample container is provided with serum and placed in the adapter the entire body portion of the sample container is received in the adapter. Thus only the lip flange of the sample container rests upon the mouth opening of the adapter.

The main body portion of the adapter can be of the same diameter as that of a standard size test tube and placed in a sample tube rack with other test tubes of standard diameter. The rack can be transported below an ultrasound detector for purposes of liquid level sensing. The ultrasound detector emits sound waves that are reflected back to the detector as echoes from only the mouth portion of the sample container and the liquid level within the sample container.

Any ultrasonic waves that reach the tapered body portion of the adapter are reflected away from the sound detector. Therefore, the sound detector does not receive any echoes from the adapter and consequently does not recognize any surfaces of the adapter. The adapter is thus essentially invisible to the ultrasound detector.

Since the lip flange of the sample container is always at the same position in the adapter the sound detector can always recognize the lip flange of the sample container based on the echo it produces. The only other echo received by the sound detector is from the liquid level surface which is always below the lip flange of the sample container. Therefore the sound detector can clearly distinguish between the echo from the liquid level surface and the echo from the lip flange of the sample container. The sound detector can also clearly distinguish any echoes from the sample rack, which are substantially weaker than the echoes from the sample container and the liquid level.

Since no other echoes from the adapter or the sample container are received by the sound detector the adapter provides a reliable means for facilitating the sensing of liquid level in the sample container.

The invention accordingly comprises the constructions and methods hereinafter described, the scope of the invention being indicated in the claims.

DESCRIPTION OF THE DRAWINGS

In the drawings,

FIG. 6 is a sectional view thereof taken on line 6—6 of FIG. 5;

FIG. 7 is an exploded view thereof;

FIG. 8 is an enlarged exploded sectional view thereof without the sample container;

FIGS. 10 and 11 are elevational views, partly shown in section, of a prior art sample container support system during ultrasound liquid level sensing;;

FIG. 12 is a simplified perspective view of another embodiment thereof;

FIG. 13 is an enlarged sectional view thereof;

FIG. 14 is an exploded view thereof;

FIG. 15 is a sectional view thereof taken on the line 15—15 of FIG. 12;

FIG. 16 is a sectional view thereof taken on the line 16—16 of FIG. 15;

FIG. 17 is a sectional view of another embodiment thereof and;

FIG. 18 is a sectional view thereof taken on the line 18—18 of FIG. 17.

Corresponding reference characters indicate corresponding parts throughout the several views of the drawings.

DETAILED DESCRIPTION OF THE INVENTION

Figure 1:
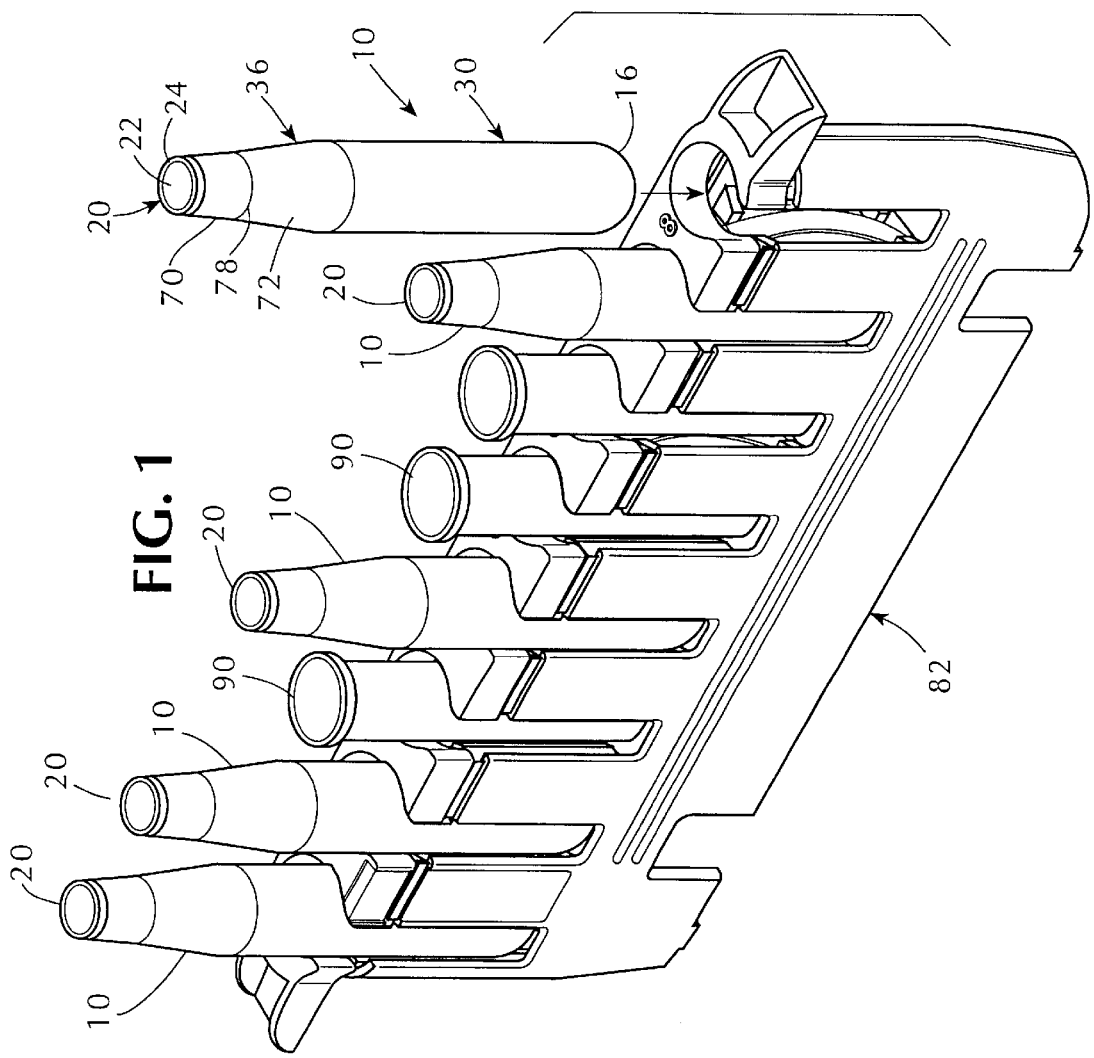
FIG. 1 is a simplified perspective view an adapter incorporating one embodiment of the invention, the adapter supporting a sample container and being shown exploded from a sample tube rack with test tubes and other similar adapters.

Referring to the drawings, especially FIGS. 1 and 4–8, an adapter incorporating one embodiment of the invention is generally indicated by the reference number 10.

The adapter 10 is a generally tubular structure preferably formed of plastic, such as clear polystyrene. The adapter 10 includes a top end with a mouth opening 12 defined by a lip portion 14 (FIG. 7) and a bottom end with a closed hemispherical portion 16.

Figure 5:
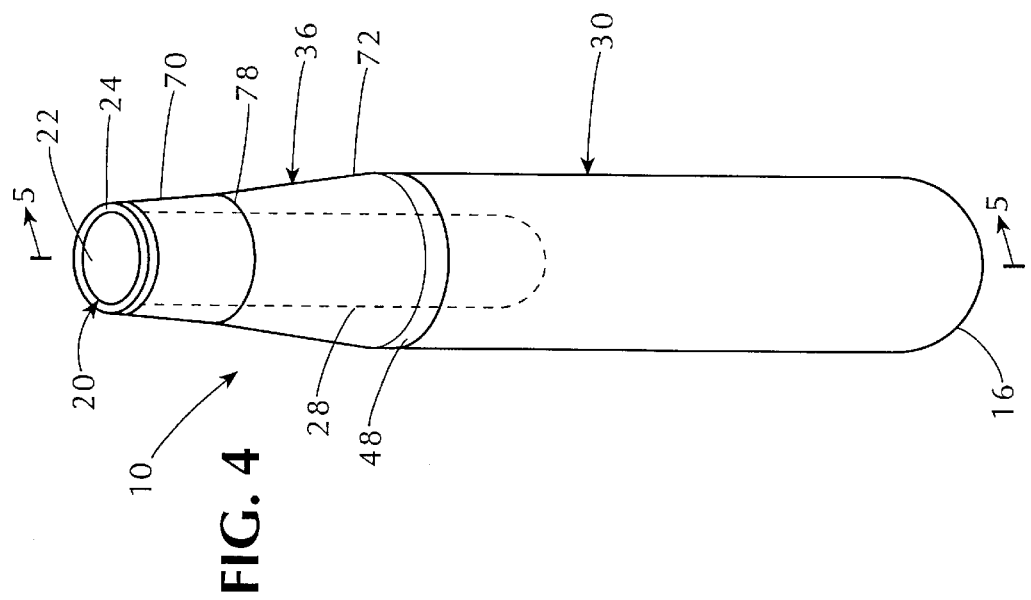
FIG. 5. is a sectional view thereof taken on line 5—5 of FIG. 4.

The mouth opening 12 of the adapter 10 is sized to accommodate a relatively small tubular sample container 20, such as a Microtainer® tube. The sample container 20 has a mouth opening 22 (FIG. 7) defined by a lip flange 24 and a closed bottom portion 26. The sample container 20 also has a body portion 28 of fixed diameter that is accommodated in the mouth opening 12 of the adapter 10 to permit the lip flange 24 of the sample container 20 to rest upon the lip portion 14 of the adapter 10 as shown in FIG. 5.

The adapter 10 has a main body portion 30 with a fixed diameter and a tapered body portion 36 that extends from the main body portion 36 to the mouth opening 12. The tapered body portion 36 has an outer wall 38 with a diameter that increases in a direction from the-mouth opening 12 toward the main body portion 30.

A joint 40 (FIG. 8) connects an upper end 46 of the main body portion 30 and a lower end 48 of the tapered body portion 36. The joint 40 includes an annular lip 42 on the main body portion 30 that projects radially outwardly from an annular recess 44 at the upper end 46 of the main body portion 30.

The joint 40 also includes an internal annular recess 50 (FIG. 8) formed at the lower end 48 of the tapered body portion 36. The annular recess 50 defines an annular ledge surface 60. An annular lip portion 54 spaced slightly below the annular ledge 60 projects radially inwardly from the annular recess 50. The annular lip portion 54 includes a generally horizontal upper surface 56 and an upwardly inclined lower surface 58.

The annular lip portion 42 on the main body portion 30 and the annular lip portion 54 on the tapered body portion 36 are sized such that the lip portion 42 is movable against the inclined lower surface 56 of the lip portion 54 with slight interference to bypass the lip portion 54 and become locked in position between the horizontal upper surface 56 and the ledge 60 of the annular recess 50 (FIG. 5).

The joint 40 connecting the tapered body portion 36 and the main body portion 30 is an inseparable snap fit joint.

The tapered body portion 36 preferably has two distinct tapered sections 70 and 72 (FIG. 8), with the tapered section 70 having a lesser amount of slope than the tapered section 72. Three equally spaced projections 74 (FIG. 8) are formed on an inner surface 76 of the tapered body portion 36 to project inwardly a predetermined amount from the inner surface 76. The projections 74 are preferably formed at a junction 78 between the tapered sections 70 and 72. The projections 74 are sized to make slight contact with the body portion 26 of the sample container 20 when the sample container 20 is positioned in the adapter 10 as shown in FIG. 5. Thus the sample container 20, when inserted in the adapter 10, is gently detented therein by engagement of the projections 74 against the body portion 26 of the sample container 20. The force of the projections 74 against the body portion 26 of the sample container 20 is easily overcome to ensure that the lip flange 24 of the sample container 20 can rest upon the lip portion 14 of the adapter 10.

Figure 9:
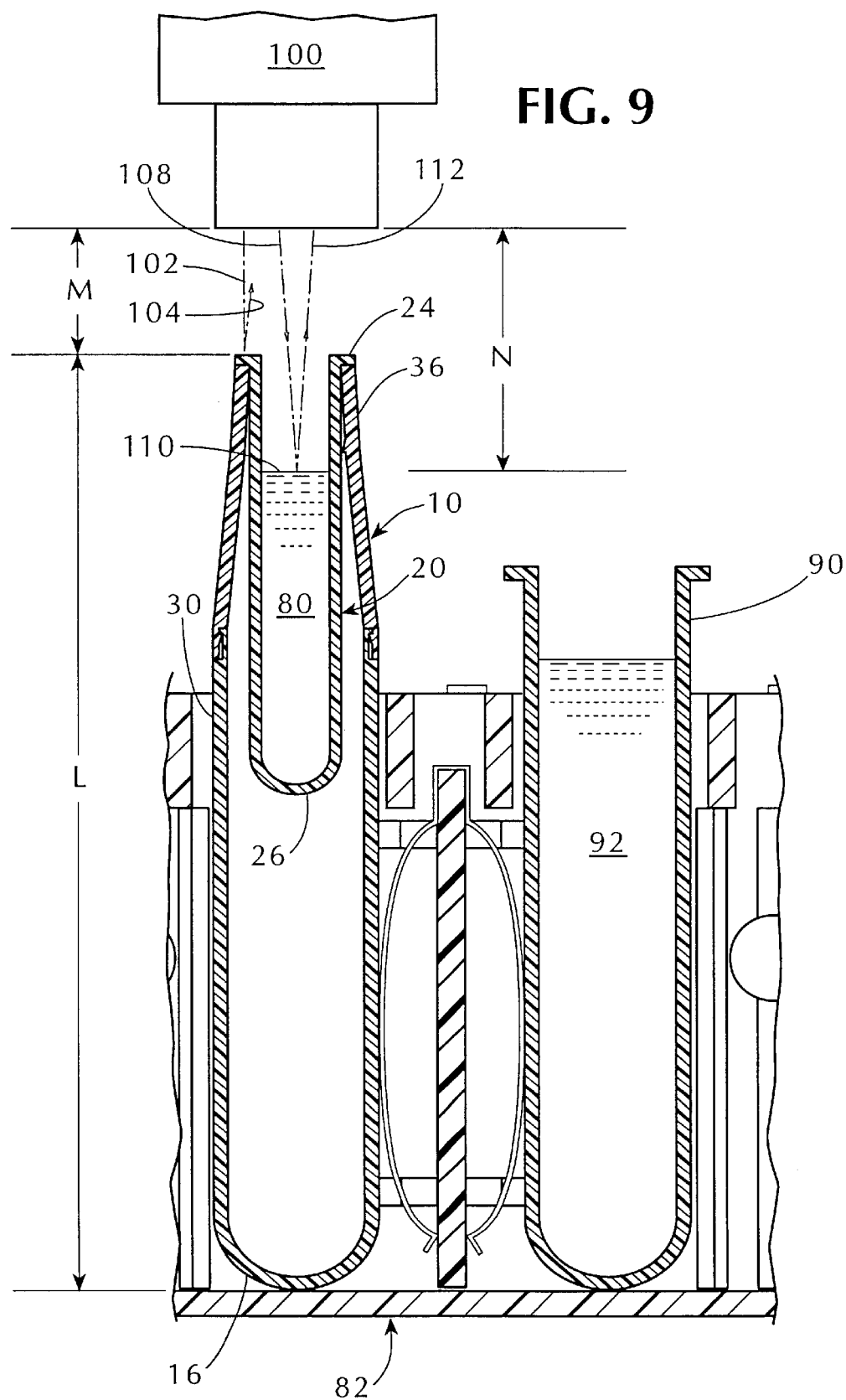
FIG. 9 is an enlarged schematic elevational view thereof partly shown in section during ultrasound liquid level sensing.

In using the adapter 10 a sample container 20 containing serum 80 that is to be subjected to sample analysis is supported in the adapter 10 as shown in FIG. 9. The adapter 10 is supported in a sample rack 82 (FIGS. 1 and 9) of the type shown in U.S. Des. Pat. 421,130. The rack 82 is adapted to be automatically transported in a sample analysis system along a known transport device 84 (FIG. 3).

Figure 2:
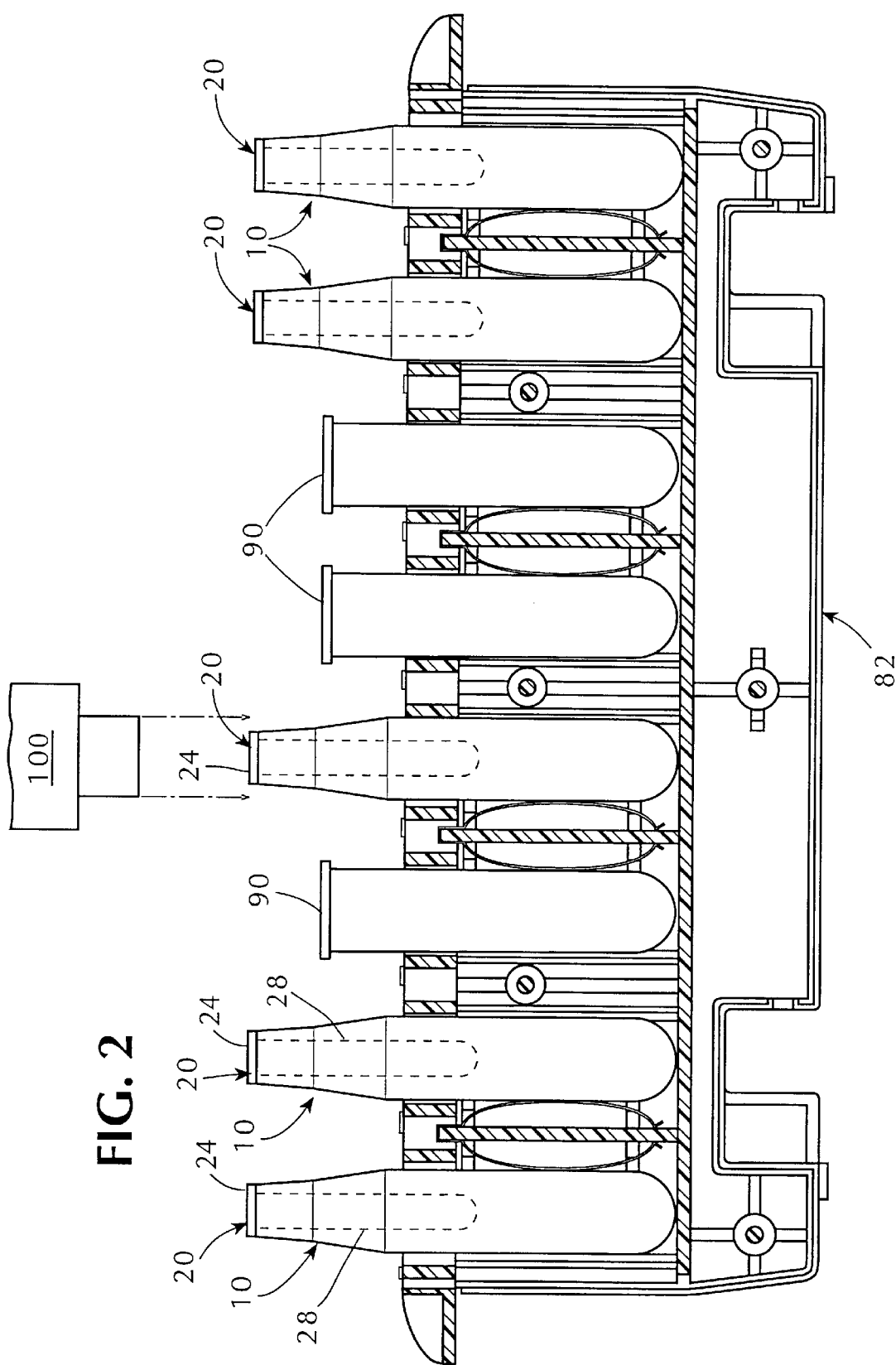
FIG. 2 is an elevational view thereof on a sample rack partly shown in section and positioned below an ultrasonic sound detector.
Figure 3:
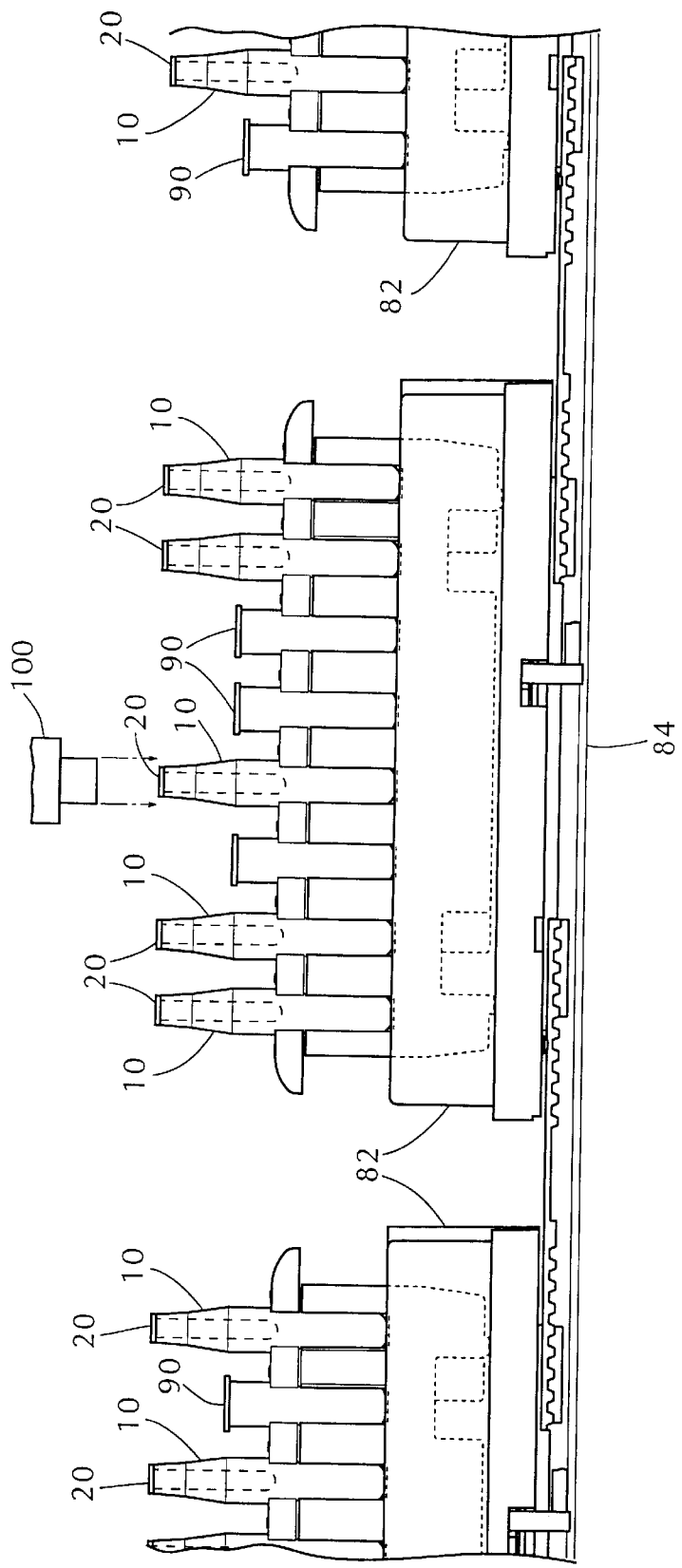
FIG. 3 is a simplified elevational view thereof in sequence with other sample racks being transported below the ultrasound detector.
Figure 4:
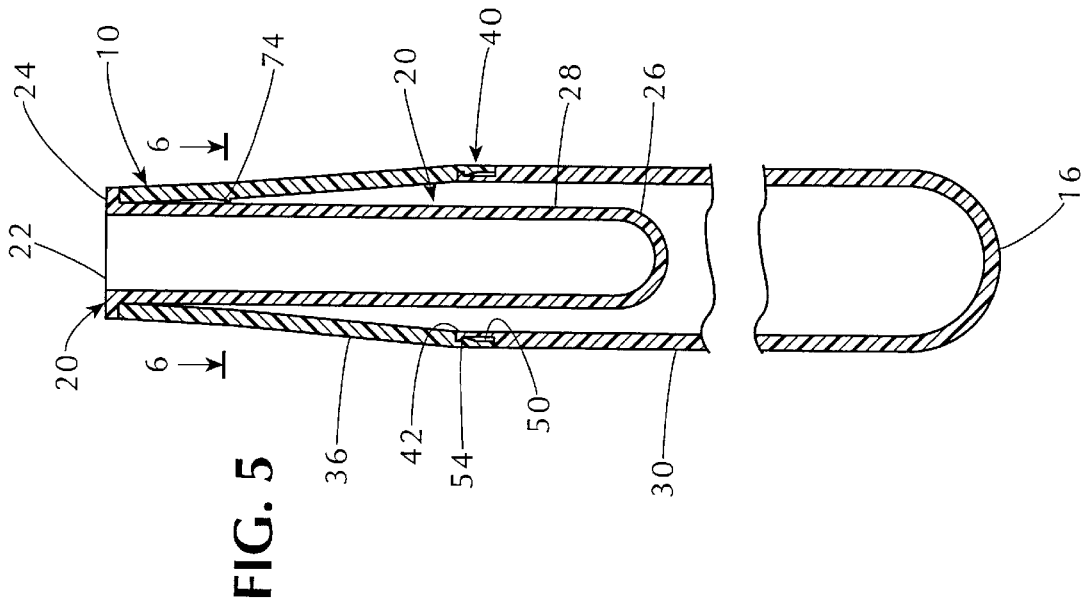
FIG. 4 is an enlarged perspective view thereof.

As shown in FIGS. 1–3 the rack 82 can hold a plurality of adapters 10, with each adapter holding a sample container 20 with serum 80. The serum 80 in each sample container 20 is usually taken from a different test subject or individual. The sample rack 82 can also hold standard size test tubes 90 containing reagents, diluents, or other materials generally indicated by the reference number 92 that are used at different locations in the sample analysis system and are transported to such locations with the sample rack 82.

During sample analysis or testing of the serum 80 in a selected sample container 20 a predetermined amount of serum is aspirated (not shown) for each test in a battery of tests that are to be performed. A measurement of liquid level 110 (FIG. 9) is made before and after each aspiration of serum sample 80 to confirm that a requisite amount of sample is aspirated and also to determine the amount of serum 80 that remains in the sample container 20 after each aspiration.

Referring to FIG. 3 the liquid level measurement is performed using a known ultrasound detector 100 that is positioned over the transport device 84 that transports the sample racks 82. Before ultrasound testing is carried out the ultrasound detector 100 is provided with a series of input parameters. For example, the lip flange 24 (FIG. 9) of the sample container 20 is always at a fixed height "L" from a selected reference level. The lip flange 24 is thus always at a fixed distance "M" from the ultrasound detector 100 (FIG. 9).

Referring to FIG. 9 the liquid level 110 of the serum 80 in the sample container 20 is always below the level of the lip flange 24. The liquid level 110 is thus always at a distance (N) from the ultrasound detector 100 that is greater than the distance (M) between the detector 100 and the lip flange 24 of the sample container 20.

The ultrasound detector 100 emits an ultrasonic wave directed, for example, at an adapter 10 that passes directly below the detector 100. When an ultrasonic wave 102 hits the horizontal surface of the lip flange 24 an echo 104 is produced and reflected back to the ultrasound detector 100. The ultrasound detector 100 can determine the distance of the echo producing surface (the lip flange 24) from the ultrasound detector 100 based on the duration of time between emission of the ultrasonic wave and reception of the echo 104.

Thus an echo 104 from the lip flange 24 of the sample container 20 will always correspond to the distance M between the lip flange 24 of the sample container 24 and the detector 100.

When the ultrasound detector 100 produces a wave 108 (FIG. 9) that reaches the liquid level 110 in the sample container 20 an echo 112 is reflected back to the detector 100. The echo 112 corresponds to the distance "N" between the liquid level 110 and the sound detector 100. Since the distance "N" differs from and is greater than the distance "M" the sound detector will recognize the distance "N" as representing liquid level.

It should be noted that the echo 112 corresponding to the distance "N" will always be within a known range of liquid levels. Thus the sound detector 100 can reliably interpret the echo 112 as corresponding to the distance "N" which represents liquid level.

Any ultrasonic waves from the ultrasound detector 100 that reach the tapered surface 38 of the tapered body portion 36 will reflect away from the sound detector 100. Thus the sound detector 100 will not receive an echo from sound waves that hit the tapered surface 38. Therefore the tapered surface 38 of the adapter 10 is essentially invisible to the ultrasound detector 100.

Under this arrangement the adapter 10 with the sample tube 20 presents only two surfaces to the detector 100 that produce a detectable echo, namely the lip flange surface 24 of the sample container 20 and the liquid level surface 110 within the sample container 20. Consequently the sound detector 100 can easily determine which of the two echoes 104 and 112 represent liquid level 110 and which echo does not represent liquid level, because the lip flange echo 104 is always constant and of lesser duration than the liquid level echo 112.

Significant problems in distinguishing liquid level are evident from the prior art sample tube support system 130 shown in FIGS. 10 and 11 wherein the sample containers 20 in FIGS. 10 and 11 each contain the same amount of the serum 80.

Referring to FIGS. 10 and 11 the known sample tube support system 130 includes a sample container 20, such as a Microtainer® tube, supported in an Easi-nest® holder 132 which in turn is supported in a Vacutainer® tube 134. The Easi-nest® holder 132 includes a tapered inner-surface 138 that bears against the body portion 26 of the sample container 20, when the sample container 20 is accommodated in the Easi-nest® holder 132.

The height of Vacutainer® tubes 34 are substantially uniform. The Easi-nest® holder 132 is of substantially uniform size and shape and dimension but the inside tapered surface 138 can deviate from a norm due to manufacturing tolerances. The sample tube container 20 is of substantially uniform dimensions. However, the amount by which sample container 20 is recessed into the Easi-nest® holder 132 can vary significantly (compare H and H' in FIGS. 10 and 11) due to tolerances of the tapered surface 138 and inconsistencies in the manual force used to push the sample tube container 20 into the Easi-nest® holder 132.

The distance K (FIGS. 10 and 11) between lip flange 140 of the Easi-nest® holder 132 and the detector 100 is substantially constant due to the uniform height of the Vacutainer® tube 134 and the uniform thickness of the lip flange 140 which rests on the mouth portion of the Vacutainer® tube 134. However, the height H of the sample tube 20 from a reference level in FIG. 10 differs from the reference level height H' of the sample tube 20 in FIG. 11 to illustrate that there is no consistency in the amount by which the sample tube 20 is pushed into the Easi-nest® holder 132. Thus the distance I between the sample tube lip flange 24 and the detector 100 in FIG. 10 is less than the corresponding distance I' in FIG. 11. Consequently similar liquid levels 110 in FIGS. 10 and 11 can have different distances J and J' (FIGS. 10 and 11) from the sound detector 100.

When the sound detector 100 receives an echo from the lip flange 24 of the sample container 20 in FIG. 10 and FIG. 11 the echoes will not be of the same duration because the lip flange 24 in FIG. 10 is at a closer distance (I) to the sound detector 100 than the lip flange 24 in FIG. 11 which is at a greater distance I'.

The sound detector 100 will also receive an echo from the liquid level surface 110 of the serum 80 in FIGS. 10 and 11. As serum 80 is depleted from the sample container 20 the liquid level 110 will approach the level of the lip flange 140 of the Easi-nest® holder 132. Thus there can be confusion between an echo from the lip flange 140 of the Easi-nest® holder 132 and an echo from the liquid level 110. The problems in sensing liquid level in the prior art sample tube support systems 130 shown in FIGS. 10 and 11 are manifest because the systems 130 present at least three horizontal surfaces that reflect echoes back to the sound detector 100, namely the lip flange 24 of the sample container, the liquid level 110 and the lip flange 140 of the Easi-nest® holder. Since the echo produced by the liquid level 110 can be confused with the echo produced by the lip flange 140 of the Easi-nest® holder liquid level sensing in the prior art sample tube support system 130 shown in FIGS. 10 and 11 is not reliable.

A sample tube adapter incorporating another embodiment of the invention is generally indicated by the reference number 150 in FIG. 12.

The sample tube adapter 150 includes a main body portion 152 and a tapered body portion 154. An upper end of the main body portion 152 and a lower end of the tapered body portion 154 include complementary shaped step portions 156 and 158. An ultrasonic welding ridge 160 is provided at one of the step portions such as the step portion 158. The main body portion 152 and the tapered body portion 154 of the sample tube adapter 150 are connected by ultrasonic welding of the step portions 156 and 158 in a known manner. The sample tube adapter 150 is otherwise structurally similar to the sample tube adapter 10 and supports a sample container 20 in the same manner as the sample tube adapter 10.

Still another embodiment of the sample tube adapter is generally indicated by the reference number 170 in FIG. 17. The sample tube adapter 170 is a one piece structure that includes a bottom opening 172, a tapered body portion 174 and a main body portion 176. The adapter 170 is otherwise similar in structure to the adapter 10 or the adapter 150 and supports a sample container 20 in the same manner as the sample tube adapter 10.

Some advantages of the invention evident from the foregoing description include a sample tube adapter that supports a sample container at a constant known elevation. The adapter and sample container reflect back to an ultrasound detector only one echo from a structural surface, namely the lip flange of the sample container and only one echo from the liquid level in the sample container that is supported by the adapter. Thus the ultrasound detector can reliably distinguish liquid level from the lip flange since the echo from the liquid level is always of longer duration than the echo from the lip flange.

Another advantage of the invention is that the adapter has a tapered surface that deflects any ultrasound waves that hit the tapered surface away from the sound detector so that the sound detector does not detect any echoes from the tapered surface portion of the adapter. No other surface portions of the adapter reflect echoes back to the ultrasound detector. The adapter is thus invisible to the ultrasound detector. Still another advantage of the invention is that the adapter will always support the sample container at a consistent known height. Another advantage of the adapter is that it directly supports the sample container and eliminates the need for any intermediate support device between the sample container and the adapter. A further advantage is that the adapter provides a simple and novel method for liquid level sensing, eliminates guess work and confusion and is thus more reliable than known prior art methods for sensing liquid level in a sample container.

In view of the above it will be seen that the several objects of the invention are achieved and other advantageous results attained. As various changes can be made in the above constructions and methods without departing from the scope of the invention it is intended that all matter contained in the above description or shown in the accompanying drawings shall be interpreted as illustrative and not in a limiting sense.

What is claimed is:

1. A method of ultrasonically sensing liquid level in a sample container comprising,
   a) forming an adapter with a mouth opening and a tapered body portion that extends below the mouth opening, the mouth opening being sized to hold an open-mouthed sample container,
   b) forming a main body portion of the adapter to extend below the tapered body portion with a main body diameter that is larger than the mouth opening of the adapter to permit accommodation of the adapter in a sample tube rack,
   c) placing the sample container in the mouth opening of the adapter such that a lip flange of the sample container rests on the mouth opening of the adapter,
   d) placing the adapter with the sample container in a sample tube rack such that the elevation of the lip flange of the sample container in the adapter is at a known height from a reference level,
   e) providing an ultrasound detector at a predetermined elevation above the lip flange of the sample container when the adapter and sample container are supported in the sample tube rack,
   f) directing a first ultrasonic wave from the ultrasound detector at the sample container and identifying a first ultrasonic echo from the sample container lip flange based on a known distance between the ultrasound detector and the lip flange of the sample container,
   g) directing a second ultrasonic wave from the ultrasound detector at liquid level in the sample container and identifying a second ultrasonic echo as corresponding to the liquid level in the sample container based on known characteristics of the first ultrasonic echo and on a difference between the second ultrasonic echo and the first ultrasonic echo because there is a greater distance between the ultrasound detector and the liquid level than between the ultrasound detector and the lip flange of the sample container, and
   h) allowing the tapered surface of the adapter to deflect any ultrasonic echoes from the tapered surface away from the ultrasonic detector, whereby the adapter permits echo reflection back to the ultrasonic detector of only the first and second ultrasonic waves.

* * * * *